United States Patent
Fichet et al.

(10) Patent No.: US 7,218,396 B2
(45) Date of Patent: May 15, 2007

(54) METHOD AND APPARATUS FOR SPECTROSCOPY OF THE OPTICAL EMISSION OF A LIQUID EXCITED BY A LASER

(75) Inventors: Pascal Fichet, Poissy (FR); Jean-Luc Lacour, Villebon sur Yvette (FR); Annie Rivoallan, Villebon sur Yvette (FR)

(73) Assignees: Commissariat a l'Energie Atomique, Paris (FR); Compagnie Generale des Matieres, Velizy Villacoublay (FR)

( * ) Notice: Subject to any disclaimer, the term of this patent is extended or adjusted under 35 U.S.C. 154(b) by 91 days.

(21) Appl. No.: 10/529,127

(22) PCT Filed: Aug. 20, 2003

(86) PCT No.: PCT/FR03/50033

§ 371 (c)(1),
(2), (4) Date: Aug. 19, 2005

(87) PCT Pub. No.: WO2004/029598

PCT Pub. Date: Apr. 8, 2004

(65) Prior Publication Data

US 2006/0119846 A1    Jun. 8, 2006

(30) Foreign Application Priority Data

Sep. 24, 2002  (FR) .................................. 02 11766

(51) Int. Cl.
*G01N 21/63*    (2006.01)
*G01N 21/71*    (2006.01)

(52) U.S. Cl. ..................................................... 356/318
(58) Field of Classification Search ................ 356/317, 356/318
See application file for complete search history.

(56) References Cited

U.S. PATENT DOCUMENTS 5,583,634 A    12/1996    Andre et al.

FOREIGN PATENT DOCUMENTS

WO    WO 02/063284 A2    8/2002

OTHER PUBLICATIONS

Aragon C. et al., "Determination of Carbon Content in Molten Steel Using Laser-Induced Breakdown Spectroscopy"; Applied Spectroscopy, The Society for Applied Spectroscopy. Baltimore, US, vol. 47, No. 5, May 1, 1993, pp. 606-608, XP000363249, ISSN: 0003-7028.
Rusak D. A. et al., "Fundamentals and Applications of Laser-Induced Breakdown Spectroscopy"; Critical Reviews in Analytical Chemistry, CRC Press Inc., Boca Raton, FL, US, vol. 27, No. 4, 1997, pp. 257-290, XP001090876, ISSN: 1040-8347.
Int'l Search Report for PCT/FR03/50033.

*Primary Examiner*—F. L. Evans
(74) *Attorney, Agent, or Firm*—RatnerPrestia

(57) ABSTRACT

A method for spectroscopy of the optical emission of a liquid excited by a pulsed laser focused on the surface thereof is such that the area of analysis is scanned by a laminar discharge of gas whose velocity and section are such that it is possible to remove the residues of the plasma suspended in the gas, resulting from a first laser pulse, before the subsequent laser pulse occurs.

11 Claims, 2 Drawing Sheets

US 7,218,396 B2

METHOD AND APPARATUS FOR SPECTROSCOPY OF THE OPTICAL EMISSION OF A LIQUID EXCITED BY A LASER

This application is the U.S. national phase application of PCT International Application No. PCT/FR2003/050033, filed Aug. 20, 2003, and claims priority of French Patent application No. 02/11766, filed Sep. 24, 2002.

FIELD OF THE INVENTION

The present invention relates to a process and to a apparatus for spectroscopy of the optical emission of a liquid excited by a laser.

It is known that the analysis of a compound by optical emission spectroscopy can use an energy input applied to the compound analyzed by means of a laser beam producing radiations proper to various components of the compound, thus making it possible to identify the latter and their respective concentrations.

More precisely, this energy input produces a plasma made up of the chemical elements present in the analyzed compound, the luminous radiation of which is made up of rays of frequencies inherent in the nature of the components, whereas their intensity is determined by the concentration of the latter.

Such a process makes it possible to perform quick analyses since the determination of the concentration of several elements in the liquid being performed simultaneously.

Moreover, it requires minimum preparation of the compound and it permits obtaining an analysis resolution for detecting the components at concentrations amounting to as little as one particle per million (ppm).

Furthermore, this process permits generating a minimum of effluents or wastes, since only the small amount of compound being analyzed before needs to be considered regarding its recycling or its elimination.

However, such analysis is complex when the compound analyzed is physically modified by the impact of the laser beam. This is so when the compound is a liquid and the laser beam is applied to its surface, as described in the document entitled, "panoramic laser-induced breakdown spectrometry of water" by Messrs. Charfi and Harith, published in Spectrochimica Acta Part B: Atomic Spectroscopy, Jul. 31, 2002, vol. 57, No. 7, pp. 1141 to 1153.

In fact, as indicated in this document, the impact of one pulse of laser beam on the surface of a liquid produces, on the one hand, splashes which attenuate by their opacity the following pulses of the light beam and which are pollutants to the optical system measuring the radiation resulting from the interaction and, on the other hand, wavelets and shock waves at the surface of the liquid being analyzed, which defocus the beam.

Now, some of such splashes arrest the essential of the light energy before it interacts with the jet of liquid being analyzed, which causes modifications of the optical emissions measured, although the composition of the liquid analyzed is constant.

For their part, the shock wavelets and waves at the surface of the liquid being analyzed defocus the laser beam, which also modifies the radiation emitted by the surface impacted by the light beam on this liquid.

In other words, the splashes outside of the jet and the disturbances at the surface increase the separation measured between successive analyses, consequently reducing the accuracy of the analysis.

To limit these inhomogeneities it is possible, as described in the document previously cited, to optimize the conditions of manipulation by tilting the laser beam with respect to the surface of the liquid so as to limit the impact of the beam on the surface.

Furthermore, a low frequency of repetition or recurrence, of the order of 0.2 Hz, is utilized to limit again the wavelets at the surface of the liquid analyzed, whereas the analyses on solids, which do not have these problems, are performed at recurrence frequencies of 10 to 20 Hz.

Such surface problems can interfere with analyses such as the one cited by Nai-Ho Cheung and Edward S. Yeung in the document entitled "Distribution of sodium and potassium within individual human erythrocytes by pulsed laser vaporization in a sheath flow," published in Analytical Chemistry 1994, 66, pp. 929 to 936.

In this document there is proposed an apparatus 100 (FIG. 1) permitting the analysis, by laser excitation or ablation coupled with optical emission spectroscopy, of liquid 110 issued from a cell, this liquid presenting the difficulty of being available in too small a quantity to permit correct focusing of the laser beam on its surface.

To permit the analysis of this liquid 110, it is transmitted by capillarity in a duct 112 coming in contact with the walls of a duct of larger size 114, this second duct 114 transmits a liquid 116 which transports the liquid 110 that issued from the cell.

The duct 112 brings the liquid 110 being analyzed against the wall of the duct 114 such that, by capillarity, the liquid 110 being analyzed is at the surface of the liquid 116 that issued from the duct 114.

Thus, an analysis of the compounds situated at the surface of the liquid 118, liquid mixture 110 and 116, leads to an analysis of the liquid 110.

To perform an analysis of a liquid without having to deal with the problems mentioned above, it is known to generate the plasma radiating into the interior of the liquid being analyzed, as described by David A. Cremers, Leon J. Radziemski, Thomas R. Loree, in the document entitled, "Apparatus and method for spectrochemical analysis of liquids using the laser spark," in U.S. Pat. No. 4,925,307 published 15 May 1990.

In this document its authors mention the problems mentioned above in connection with the analysis of a liquid, inherent in the focusing of the laser beam on the surface of the liquid and proposing the analysis of this liquid by generating, with the aid of a first laser, a plasma in the interior of the liquid being treated, that is, by focusing the laser beam inside of the liquid.

In a second step a second laser focused into the plasma produces the emission of light, the analysis of which constitutes the measurement.

Such a procedure involves the problem of requiring a precise positioning of the optics and a complex synchronization of the laser beams.

In other words, this process requires perfect mechanical stability of the system and presents great complexity and cost.

Furthermore, it is known that optical analysis by spectroscopic beginning with laser excitation can be improved when the product analyzed, i.e., receiving the laser beam, is in a specific gaseous environment.

For example, in document entitled, "Determination of colloidal iron in water by laser-induced breakdown spectroscopy" presented by Yoshiro Ito, Osamu Ueki, Susumu Nakamura in Analytica Chimica Acta 199 (1995), pp. 401–405, the authors compare the properties of a helium, air or argon environment of a liquid to improve the spectroscopy of the emissions produced by the laser beam excitation of the latter.

In this document the authors cited describe the use of an apparatus 200 (FIG. 2) comprising a duct 202 carrying a liquid 206 which is later surrounded by a gas 208 whose effect on the emission of the rays from the plasma generated by laser in the liquid 206 is studied. The laser beam is orthogonal to the surface of this liquid.

By making the liquid being analyzed to flow in jet form, this apparatus enables the laser beam to strike a different portion of this liquid on each laser pulse, which limits the effect of the wavelets and shock waves.

Furthermore, the analyses are made without problem of contamination of walls of the container of the cells, since the liquid is analyzed only at the outlet of the duct.

According to this document it was found that an argon (Ar) or helium (He) environment had different effects on the intensity of the signals; the argon increasing their intensity whereas helium reduced it.

This document also discloses that the temperature of the plasma, important to the quality and the accuracy of the signal analyzed could be kept high in spite of any low thermal conductivity of the gas surrounding it.

The invention results from the finding that in all the former techniques described above, the plasma resulting from the interaction of a laser beam pulse with the jet of liquid under analysis violently hurls microdroplets at very high velocity in all directions, which greatly interfered with the measurements and harms the accuracy of the analysis.

In fact, since microdroplets of liquid are in suspension around the plasma formed by a first laser beam, they disturb any new use of the laser beam on the surface.

Since then, the various pulses of the laser beam applied to the surface of the liquid are attenuated erratically by the cloud of micro-droplets projected by a preceding pulse, and consecutive analyses of the liquid show differences caused by these microdroplets. In other words, the repeatability and accuracy of the analyses are limited by these microdroplets.

The present invention aims to remedy this difficulty.

SUMMARY OF THE INVENTION

More precisely, the invention consists of a process for the optical emission spectroscopy of a liquid excited by a pulsed laser focused on its surface, characterized in that the area of analysis is swept by a laminar flow of gas having sufficient speed and cross section to eliminate the residues of the plasma suspended in the gas resulting from a first laser pulse before the following laser pulse takes place.

The gas thus has a function of sweeping away the residues of a preceding plasma, and also of contention on the liquid whose surface is stabilized, which contributes also to the repeatability of the analyses.

Otherwise, if the gaseous environment is determined, and the focusing of the light rays is accomplished, no modification of the lens or of the arrangement of the installation is any longer necessary, even when the liquid being analyzed is changed, except, if such be the case, if one of these liquids has a viscosity very different from the others. This absence of adjustments during analyses increases the repeatability and the repeatability of the analyses.

Furthermore, it is preferable for the gas for eliminating residues to be chosen from among gases which improve the radiation generated when the analysis is performed.

The invention thus concerns a method for optical emission spectroscopy of a liquid excited by a pulsed laser focused on its surface, a gas being arranged in the vicinity of the zone of analysis including this surface, characterized in that the gas is given a laminar sweeping movement parallel to the surface being analyzed, this movement having sufficient velocity to eliminate the residues in this gas of the plasma produced by a preceding laser pulse and having a sufficient cross section to eliminate the residues of the plasma that are suspended in the gas.

In one example of embodiment, the gas disposed near to the liquid of the zone of analysis produces a contention effect on the free surface of this liquid.

The velocity of the gas is determined according to at least one of the following characteristics of the liquid analyzes: its temperature, its viscosity, its rate of flow, the turbulent or laminar nature of its flow.

The section swept by the laminar flow of the gas is determined according to at least one of the following characteristics: speed of expansion of the plasma, rate of recurrence of the laser pulses, and accuracy of the measurement.

Preferably the liquid is flowing in the zone of analysis.

In one embodiment the gas is carried into the zone of analysis by a duct surrounding the duct carrying the liquid under analysis.

The gas used is, for example, argon or helium.

The radiation issued by the plasma of interaction between the liquid being analyzed and the laser beam is, in a preferred embodiment, collected colinearly with the laser beam.

The zone of analysis and the means for generating a jet of the liquid to be analyzed and a jet of gas surrounding it can be removed into an air-tight chamber able to contain dangerous products or a hostile environment and confine them. In this case the colinearity of the radiation emitted by the plasma of interaction between the liquid being analyzed and the laser beam is particularly advantageous, for it permits using only one porthole for the enclosure.

Preferably, the laser beam is inclined with respect to the plane formed by the surface of the analyzed fluid at an angle other than 90 degrees.

It is preferable that, when the liquid is flowing, the point of impact of the laser beam on the jet is close to the outlet of the liquid from a duct. For example, this distance is between 5 and 15 mm for water. In fact, after a certain distance depending on the velocity of flow of the liquid, the jet becomes unstable and then diverges.

The invention also concerns an optical emission spectroscopy apparatus for a liquid excited by a pulsed laser focused on the surface of this liquid, characterized in that it comprises:

a laser able to generate pulses of coherent light with a power density of at least 1 $Gw/cm^2$, means for generating a laminar jet of the liquid being examined, of a length of at least one centimeter, means for generating a laminar jet of gas parallel to the surface of the liquid being analyzed, and in contact therewith, means for focusing the laser beam into the zone of analysis, on the surface of the jet of liquid being analyzed, a means for collecting the light resulting from the interaction of the light pulses of the laser with the jet of liquid being analyzed, a spectroscope able to operate in the range of frequencies at which the rays of emission of the liquid being analyzed are found, and arranged so as to receive the light of interaction collected by the bundle of optical fibers, means for circulating the examined liquid in jet form, and means for circulating the gas in jet form that must flow tangentially to the analyzed liquid.

According to an embodiment, the means for gathering the light emitted by the liquid being examined is such that this light is gathered colinearly with the excitation laser beam, and the apparatus has an air-tight enclosure in which the liquid to be analyzed and the means for generating the laminar gas, jet, the colinearity of the excitation laser beam and of the direction of the collected light permit the use of a single porthole of the enclosure for the laser beam and the collected light.

BRIEF DESCRIPTION OF THE DRAWINGS

Other characteristics and advantages of the invention will appear with the detailed description of an embodiment made hereinbelow as a non-restricting example, by referring to the annexed drawings in which.

DETAILED DESCRIPTION

Figure 3:
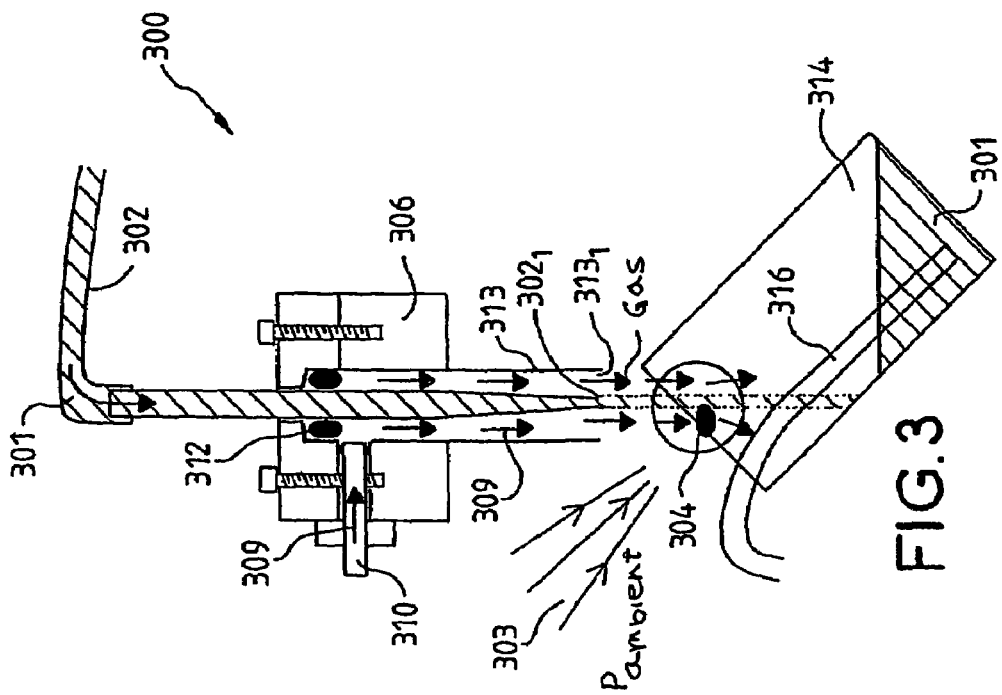
FIG. 3 represents in detail an ablation cell, i.e., an apparatus for spectroscopic analysis of optical emission using an excitation laser, according to the invention.

The apparatus 300 described below with the aid of FIG. 3 permits the performance of a process, pursuant to the invention, of the analysis of a liquid 301 by optical emission spectroscopy generated by means of a laser beam 303 focused on the surface of the liquid 301.

For this purpose, properties of speed and rate of flow are conferred upon a gas 309 in the analysis zone 304 comprising this liquid surface, such that the disturbances generated by the impact of the laser beam on the surface of the liquid are minimized. The velocity and rate of flow of the gas 309 must be of values sufficiently high to eliminate the microdroplets. However, this velocity and this rate of flow must not exceed a certain limit so as not to disturb the flow of the liquid jet. The pressure of the gas feeding the apparatus is controlled in order to adjust the speed and rate of flow.

The ablation cell 300, which can be discharged into an enclosure able to contain and confine a hostile environment, includes a duct 302 directing the liquid 301 to be analyzed to an analysis zone 304, that is, a zone including the surface of the liquid 301 onto which a laser beam to be described later on is focused.

This liquid duct 302 crosses a support 306 for connection to a duct 310 bringing in gas 309, such as nitrogen or argon. This support 306 enables the gas 309 to be distributed all around the liquid duct 301 and to bring it out through a duct 313 of the same axis as duct 301 and surrounding it. This duct 313 exits through an orifice $313_1$ with diameter $D_1$, and the liquid duct 302 discharges through an orifice $302_1$ of diameter $D_2$. Inside of the support 306 sealing means 312 are placed between the latter and the liquid duct 302, at a level situated between the end of this duct 301 in the support and the inlet duct 310 in order to force the gas to escape toward the analysis zone 304.

Dud 302 is a Pasteur pipette having an outlet orifice $302_1$ of a diameter $D_2$ of 0.1 mm, and the duct 313 is a tube of inside diameter $D_1$ of 10 mm.

The velocity and rate of flow (the pressure in the example) of the gas 309 must not exceed the limit beyond which this gas might deflect the jet of fluid 301 to be analyzed in zone 304, or make it fluctuate, which would defocus the laser beam and would make the analysis lose its precision. It is easy to determine this threshold experimentally for each pair of liquid to be analyzed and gas. For example, when the liquid to be analyzed and the gas is air or nitrogen, the limit is 1 bar.

When the liquid is water and the gas is air or nitrogen, this effect is obtained by feeding the inlet duct 310 with gas under a pressure $P_{gas}$ greater than the ambient pressure $P_{ambient}$ of 0.15 at 1 bar, and preferably 0.2 bar.

This effect of scanning must be adapted to the physical characteristics of the solution and of the gas, and especially its viscosity. For example, if the liquid to be analyzed is an oil having a cinematic viscosity at 100EF of 67.6 cst and the gas is air or nitrogen, the pressure required in the gas inlet duct 310 must reach 0.4 bar above the ambient.

When the gas pressure satisfies these conditions, this gas stabilizes the jet by a contention effect, and drives away from the analysis zone 304 the microdroplets formed around the plasma, such that the latter do not disturb the action of the laser on the liquid when another light pulse arrives, which is significant since these pulses are at least one second apart.

Such a reduction of the disturbances has made it possible to improve the signal-to-noise ratio by about a factor of 100 with respect to the use of the gas at ambient pressure. This improvement is perceived, depending on the modalities selected by the operator, both in a great improvement of the accuracy and repeatability of the measurements for the same rate of repetition of the laser pulses, and in a great improvement of the rate of repetition of the laser pulses, to the degree that the laser permits, and also in a simultaneous, but less important, improvement of each of these parameters.

In the analysis zone 304, the gas 309 in laminar flow eliminates the microdroplets in suspension after the impact of a pulse of the laser beam and stabilizes the surface of the liquid 301 under analysis.

Lastly, the apparatus described in this example presents arrangements known in closely related contexts. In particular, it is known that, for a liquid at rest, the laser beam can be tilted in relation to the surface of this liquid at an angle other than 90°, so as to limit the disturbances engendered by the laser beam. In the example, this angle is greater than 60° and less than 90°.

Furthermore, since the liquid analyzed is flowing in the analysis zone, the bubbles formed in the liquid by the laser beam are removed from this zone by the flow.

In this embodiment the liquid 301 is collected in a vessel 314 provided with a duct 316 one end of which is introduced into the liquid 301 at the start of operation.

The duct 316 is connected to a pump 418 (FIG. 4) such that it is possible to recycle the fluid 301 so as to use but a limited amount of liquid for performing the analyses.

Furthermore, the focus of the laser and of the optical system for recording the emissions can be fixed throughout all of the analyses. Then the analysis apparatus is particularly stable, again improving the repeatability of the analyses.

As indicated before, the gas 309 permits obtaining a very repeatable and stable plasma. It is then possible to use repeat or recurrent frequencies for the laser from 10 to 20 Hz, or more, for a period of several minutes. This permits obtaining high spectroscopic accumulation periods, and hence improving the signal-to-noise ratio.

Figure 4:
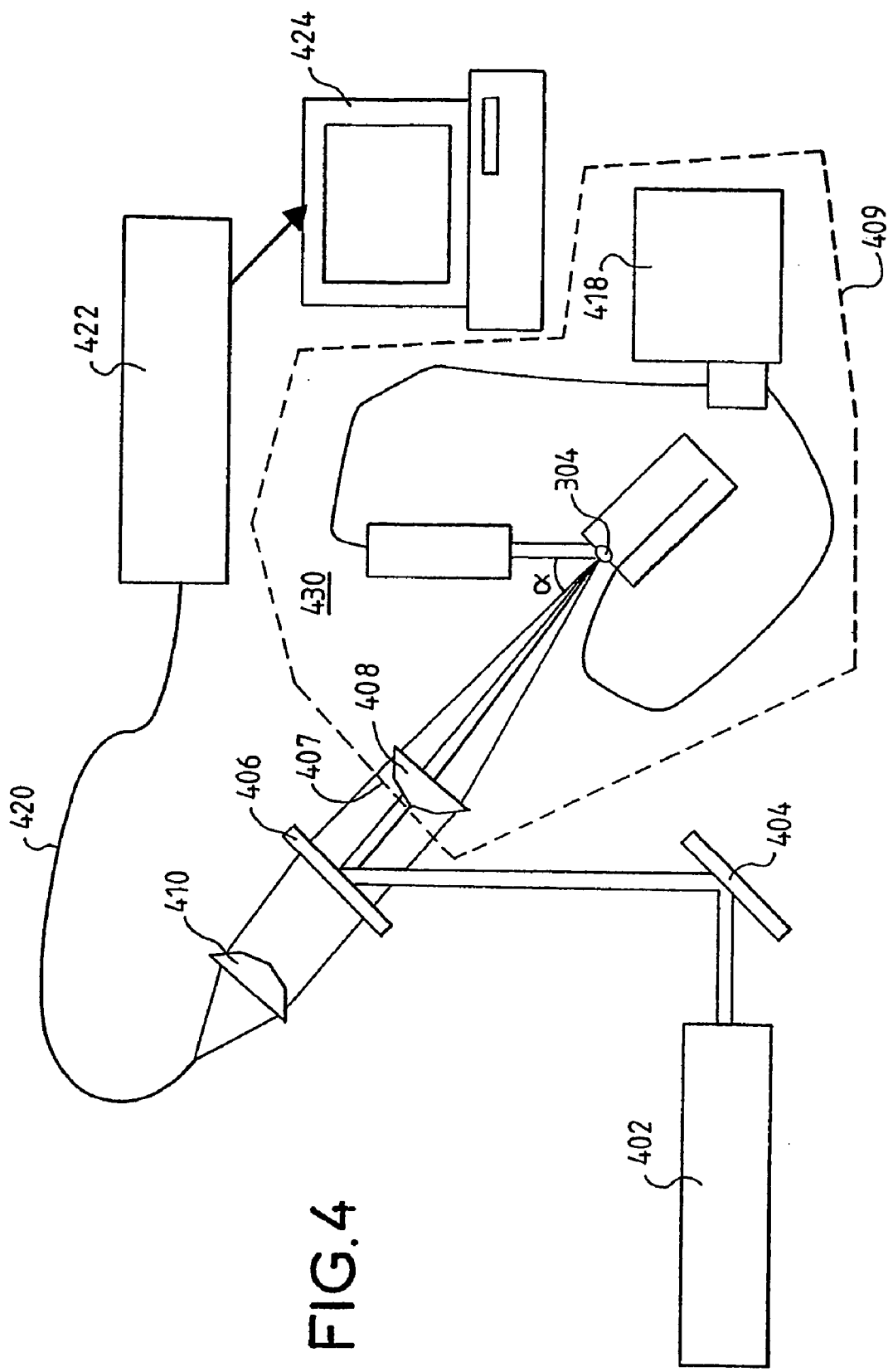
FIG. 4 represents an embodiment of the apparatus shown in FIG. 3.

The apparatus represented in FIG. 4 comprises a laser 402 emitting beams at a fundamental wavelength of 1064 nm, to which is added a frequency doubler bring this wavelength to 532 nm. It also comprises a glass dichroic mirror 404, a quartz dichroic mirror 406 and a convergent lens 408 to aim and focus the laser beam on the surface of the liquid to be analyzed in the analysis zone 304.

In this example, the laser 402 is an Nd-YAG laser of wavelength 1064 nm, reduced to 532 nm by a frequency doubler, and emitting pulses with a duration of seven nanoseconds. Any pulse rate of the order of 2 to 30 ns is also appropriate as long as the specific power delivered to the jet for analysis is at least 1 Gw/cm$^2$.

Given the elimination from the gas of the residues of the preceding plasma and the stabilization of the surface of the liquid being analyzed, the laser can operate at a recurrent frequency of ten of twenty Herz so as to perform a large number of analyses for a given period, thus improving the repeatability of this analysis.

Furthermore, it should be pointed out that the quartz dichroic mirror 406 permits transmitting analytical rays in the ultraviolet range.

The radiation emitted by the plasma in this analysis zone is guided up to an optical fiber bundle 420, which can be reduced to a single optical fiber, by the convergent lens 408 formed of a single lens, the mirror 406, then a convergent optic 410 thus formed of a single lens. Bundles of fibers called split section/bundle transformers, which permit gathering an approximately circular light spot, and apply it almost without loss to the input slot of a spectrometer. The material of these fibers should permit the transmission of all the rays emitted by the liquid being analyzed.

The bundle of optical fibers 420 is here reduced to a single fiber, of silica, of one millimeter diameter and about ten meters of length.

Figure 2:
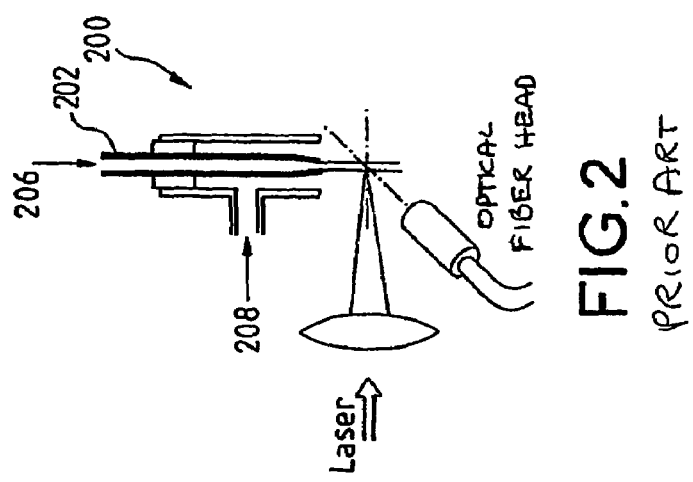
FIGS. 1 and 2 already described represent known apparatus for spectroscopic analysis of optical emission using an excitation laser.
Figure 1:
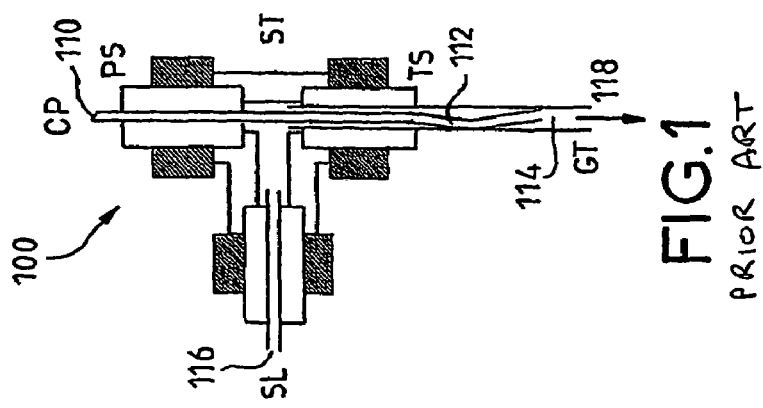

Unlike the apparatus of the prior art (FIG. 2), this fiber collects the spectrum of interaction radiated by the plasma along the same axis as the laser beam incident on the zone 304, which contributes to establishing the signal. In fact, this colinearity permits maintaining the existence of the signal if the position of the point of impact of the laser beam varies under the effect of the plasma.

This characteristic maximizes the light gathered when the laser beam is not perpendicular to the surface of the liquid. Moreover, it favors the use of the apparatus in hostile environments, such as a vacuum or a nuclear environment, by reason of the possibility of passing the excitation laser beam and the light spectrum gathered through a one and only port 407 of the protective and confining enclosure 409 represented by broken lines.

Application to radioactive solutions used in the nuclear power industry constitutes a privileged application. In this case this enclosure 409 represents the walls of a "hot cell" of the nuclear industry, and the port 407 is preferentially made of quartz.

The gathering of light by means of a fiber optic permits working remotely and saves the user of the apparatus from having to be close to the zone where the radioactive (or toxic, or of difficult access) solutions are handled. Thus, in the case where the analysis concerns dangerous products or has to be performed in a hostile environment, it is possible to situate the ablation cell 430, defined by the line 409, in the hazardous environment, while keeping the rest of the apparatus in an environment safe for the operators.

The possibility of performing analyses of different solutions without making any adjustment among these solutions is then particularly advantageous. Direct focusing on the spectrometer would be possible, but more complicated to adjust.

This radiation is then analyzed by a spectrometer 422, such as a Czerny Turner spectrometer or a so-called scale spectrometer connected to a computer 424 recording the emission spectra, so as to process these data.

The Czerny Turner geometry spectrometer makes it possible, with optimum adjustment, to scan a spectral range from 250 nm to 650 nm with a spectrum window for simultaneous access of 4 nm.

The scale spectrometer has the same resolution as the Czerny Turner geometry spectrometer, but its spectrum window, with the adjustment selected, covers a wavelength range of 200 to 850 nm.

Such a scale spectrometer, equipped with a CCD camera, preceded by a light intensifier, can be calibrated upon starting, since no moving part is present in the detector.

In this case, a pulse generator permits starting a window of time for measuring the radiation recorded by the camera, with a delay selected in relation to the laser pulse.

The spectrometer 422 is controlled with the aid of the computer 424 which is equipped with a data acquisition and processing software.

The analysis of various solutions is of great importance in very many industrial domains, such as the pharmaceutical, electronic, and energy industries and hostile environments. One of the privileged applications is the analysis of radioactive solutions in the nuclear energy processes.

The invention claimed is:

1. A method for the optical emission spectroscopy of a liquid excited by a pulsed laser focused on its surface, comprising the step of sweeping a zone to be analyzed by a laminar gas flow having sufficient velocity and cross sectional area to eliminate residues of a plasma suspended in the gas and resulting from a first laser pulse, before a next laser pulse takes place, so that the laminar gas flow creates a containment effect on the surface of the liquid.

2. A method in accordance with claim 1, wherein the velocity of the gas is determined according to at least one a temperature of the analyzed liquid, a viscosity of the analyzed liquid, a flow rate of the analyzed liquid, a turbulent or laminar nature of a flow of the analyzed liquid.

3. A method in accordance with one of the claims 1 or 2, wherein a cross section swept by the laminar gas flow is determined according to at least one of: a rate of expansion of the plasma, a rate of recurrence of the laser pulses, an accuracy of the measurement.

4. A method in accordance with claims 1 or 2, wherein the liquid is flowing in the zone to be analyzed.

5. A method in accordance with claims 1 or 2, wherein the gas is led into the zone to be analyzed through a conduit surrounding a conduit of the analyzed liquid.

6. A method in accordance with claims 1 or 2, wherein the laser beam is inclined in relation to a plane formed by the surface of the liquid at an angle different from 90°.

7. A method in accordance with claim 6, wherein the laser beam is inclined in relation to the plane formed by the surface of the liquid at an angle greater than 60°.

8. A method in accordance with claims 1 or 2, wherein a beam emitted by the liquid after excitation by the laser pulse is collected colinearly with the laser pulse.

9. A method in accordance with claims 1 or 2, wherein the gas is argon or helium.

10. A device for the optical emission spectroscopy of a liquid excited by a pulsed laser beam focused on a surface of the liquid, comprising:

a laser configured to generate coherent light pulses of a power density of at least 1 Gw/cm$^2$, means for generating a laminar jet of liquid to be analyzed over a length of at least one cm, means for generating a laminar gas jet parallel to the surface of the liquid to be analyzed, and in contact with the surface of the liquid, eliminating residues of a plasma suspended in the gas and resulting from a first laser pulse from the pulsed laser, means for focusing the laser beam in a zone to be analyzed on the surface of the liquid jet to be analyzed, means for collecting light resulting from an interaction of the light pulses of the laser with the liquid jet to be analyzed, a spectroscope configured to operate within a range of frequencies at which are found emission lines of the liquid to be analyzed, and being equipped so as to receive the interaction light collected by a bundle of optical fibers, means for making the liquid to be analyzed circulate in the form of a jet, and means for making the gas circulate in the form of a jet before flowing tangentially to the liquid to be analyzed.

11. A device in accordance with claim 10, wherein:

the means for collecting the emission light of the liquid to be analyzed is such that light is collected colinearly with the excitation laser beam, the device further comprises an impermeable enclosure in which are found the liquid to be analyzed and the means for generating the laminar gas jet, and the colinearity of the excitation laser beam and the direction of the collected light make possible the use of only one port of the enclosure for the laser beam and the collected light.

\* \* \* \* \*

UNITED STATES PATENT AND TRADEMARK OFFICE
CERTIFICATE OF CORRECTION

PATENT NO.       : 7,218,396 B2
APPLICATION NO.  : 10/529127
DATED            : May 15, 2007
INVENTOR(S)      : Pascal Fichet et al.

Page 1 of 1

It is certified that error appears in the above-identified patent and that said Letters Patent is hereby corrected as shown below:

Claim 2, Column 8, line 40, insert the word --of-- between the words "one" and "a".

Signed and Sealed this

Thirteenth Day of November, 2007

JON W. DUDAS
*Director of the United States Patent and Trademark Office*